United States Patent
Brewer et al.

(10) Patent No.: US 6,969,779 B2
(45) Date of Patent: Nov. 29, 2005

(54) METHOD FOR REMOVAL OF MW176 CYCLIC ACETAL FORMED DURING THE PRODUCTION OF 1,3-PROPANEDIOL

(75) Inventors: Stephen Edward Brewer, Houston, TX (US); Zaida Diaz, Houston, TX (US); Joseph Broun Powell, Houston, TX (US); Paul Richard Weider, Houston, TX (US); Glenn Charles Komplin, Houston, TX (US); Robert Lawrence Blackbourn, Houston, TX (US)

(73) Assignee: Shell Oil Company, Houston, TX (US)

( * ) Notice: Subject to any disclaimer, the term of this patent is extended or adjusted under 35 U.S.C. 154(b) by 215 days.

(21) Appl. No.: 10/676,690

(22) Filed: Oct. 1, 2003

(65) Prior Publication Data

US 2004/0087818 A1 May 6, 2004

Related U.S. Application Data

(60) Provisional application No. 60/423,140, filed on Nov. 1, 2002.

(51) Int. Cl.$^7$ .......................... C07C 27/04; C07C 29/14; C07C 31/18; C07C 27/26; C07C 29/74
(52) U.S. Cl. .................. 568/862; 568/852; 568/861; 568/868; 568/872
(58) Field of Search ............................ 568/862, 868, 568/872, 852, 861

(56) References Cited

U.S. PATENT DOCUMENTS

| 5,008,473 A | 4/1991 | Breitkopf et al. ........... 568/868 |
| 5,527,973 A | 6/1996 | Kelsey ........................ 568/862 |
| 5,786,524 A | 7/1998 | Powell et al. ................ 568/862 |
| 6,235,948 B1 | 5/2001 | Sunkara et al. .............. 568/868 |

FOREIGN PATENT DOCUMENTS

| EP | 0983985 A2 | 3/2000 | ........... C07C/29/90 |
| WO | WO 98/49216 | 11/1998 | ........... C08G/63/78 |
| WO | WO 00/10953 | 3/2000 | ........... C07C/29/80 |
| WO | WO 00/14041 | 3/2000 | ......... C07C/29/141 |

Primary Examiner—Elvis O. Price

(57) ABSTRACT

The present invention is an improvement upon the process for the production of 1,3-propanediol (PDO) wherein an aqueous solution of 3-hydroxypropanal (HPA) is formed, and the HPA is subjected to hydrogenation to produce a crude PDO mixture comprising PDO, water, MW176 acetal, and high and low volatility materials, wherein the crude PDO mixture is dried to produce a first overhead stream comprising water and some high volatility materials and a dried crude PDO mixture as a first distillate bottoms stream comprising PDO, MW176 acetal, and low volatility materials, and wherein the dried crude PDO mixture is distilled to produce a second overhead stream comprising some high volatility materials, a middle stream comprising PDO and MW176 acetal, and a second distillate bottoms stream comprising PDO and low volatility materials. The improvement on this process comprises treating the crude PDO mixture and/or the dried crude PDO mixture and/or the PDO product with an acidic zeolite, an acid form cation exchange resin, or a soluble acid to convert the MW176 cyclic acetal to more volatile materials which can be easily separated from PDO by distillation.

15 Claims, 1 Drawing Sheet

METHOD FOR REMOVAL OF MW176 CYCLIC ACETAL FORMED DURING THE PRODUCTION OF 1,3-PROPANEDIOL

This application benefit of 60/423,140 Nov. 1, 2002.

FIELD OF THE INVENTION

This invention relates to a process for the production of 1,3-propanediol (PDO) wherein an aqueous solution of 3-hydroxypropanal (HPA) is formed, and the neutralized HPA is hydrogenated to produce a PDO mixture that is distilled to produce purified PDO.

BACKGROUND OF THE INVENTION

Several companies have developed technology for the manufacture of PDO starting with ethylene oxide as the main raw material. The ethylene oxide is reacted with synthesis gas (syngas), a mixture of carbon monoxide and hydrogen, which may be obtained by steam reforming of natural gas or partial oxidation of hydrocarbons. The idealized reaction of ethylene oxide (EO) with syngas to yield PDO is shown below:

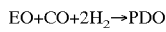

$$EO + CO + 2H_2 \rightarrow PDO$$

U.S. Pat. Nos. 4,873,378, 4,873,379, and 5,053,562 from Hoechst Celanese describe a single step reaction using 2:1 (molar) syngas at 110 to 120° C. and about 1000 psig (6900 kPa) to give 65 to 78 mole percent yield of PDO and precursors thereof. The catalyst system used consisted of rhodium, various phosphines, and various acids and water as promoters.

U.S. Pat. Nos. 5,030,766 and 5,210,318 to Union Carbide describe the reaction of EO with syngas in the presence of rhodium-containing catalysts. At 110° C. and 1000 psig (6900 kPa) of 2:1 molar syngas, a selectivity of up to 47 mole percent was achieved but the combined rate of formation of PDO and 3-hydroxy propanal was quite low at 0.05 to 0.07 moles per liter per hour. Better results were achieved by increasing the ratio of phosphoric acid promoter to rhodium catalyst.

U.S. Pat. Nos. 5,256,827, 5,304,686, and 5,304,691 to Shell Oil described PDO production from EO and syngas utilizing tertiary phosphine-complexed cobalt carbonyl catalysts. Reaction conditions of 90 to 105° C. and 1400 to 1500 psig (9650 to 10,340 kPa) of syngas (1:1 molar ratio) for three hours produced selectivities in the range of 85 to 90 mole percent and the EO conversion was in the range of 21 to 34 percent. Later work reported increased selectivity and EO conversion.

U.S. Pat. No. 5,527,973 describes a method for the purification of PDO which contains carbonyl byproducts including acetals. An aqueous solution of a carbonyl-containing PDO is formed having a pH less than 7 and then a sufficient amount of base is added to this solution to raise the pH to above 7. The solution is then heated to distill most of the water from it and then the remaining basic solution is heated to distill most of the PDO from the basic solution providing a PDO composition having a lower carbonyl content than the starting composition. This process has several steps and it would be a commercial advantage to provide a method which would lower the carbonyl content in fewer process steps.

SUMMARY OF THE INVENTION

The present invention is an improvement upon the process for the production of 1,3-propanediol (PDO) wherein an aqueous solution of 3-hydroxypropanal (HPA) is formed, and the HPA is subjected to hydrogenation to produce a crude PDO mixture comprising PDO, water, MW176 acetal (so called because it is an acetal and has a molecular weight of about 176), and high and low volatility materials, wherein the crude PDO mixture is dried, usually by distillation, to produce a first overhead stream comprising water and some high volatility materials, such as ethanol and/or process solvents, and a dried crude PDO mixture as a first distillate bottoms stream comprising PDO, MW176 acetal, and low volatility materials, and wherein the dried crude PDO mixture is distilled to produce a second overhead stream comprising some high volatility materials, a middle stream comprising PDO and MW176 acetal, and a second distillate bottoms stream comprising PDO and low volatility materials. The major part of the recoverable PDO is in the middle stream which is as much as 99.9% wt PDO. The second distillate bottoms stream may contain up to 50% wt of PDO but this PDO is difficult to separate from the low volatility materials. There may be trace amounts of MW176 acetal in the bottoms stream.

The improvement on this process comprises contacting 1) the crude PDO mixture prior to drying and/or 2) the dried crude PDO mixture prior to distillation and/or 3) the middle stream (with this third embodiment, another distillation would be required to remove the more volatile MW176 acetal reaction products from the PDO) with an acidic zeolite (for example a mordenite clay) at about 40 to about 150° C. to convert the MW176 cyclic acetal to alternate chemical species which can be more easily separated from PDO by distillation, in a process where the production of other color producing impurities and oligomers of PDO is minimized. In another embodiment of this invention, 1) and/or 2) and/or 3) are contacted with an acid form cation exchange resin, typically of the sulfonic acid type, at temperatures between ambient and about 150° C. In another embodiment, soluble acids, such as $H_2SO_4$, are used to treat the streams, preferably in a column which is resistant to corrosion, at a temperature of about 20 to about 100° C.

The contacting of the crude PDO mixture with the solid acid purifier is done as a continuous process, or batchwise, using standard methods and practice for contacting a liquid stream with a solid catalyst or adsorbent. In this manner, difficult to separate impurities such as the MW176 acetal are largely eliminated, such that PDO may be distilled to high purity with high recovery efficiencies.

DETAILED DESCRIPTION OF THE INVENTION

Figure 1:
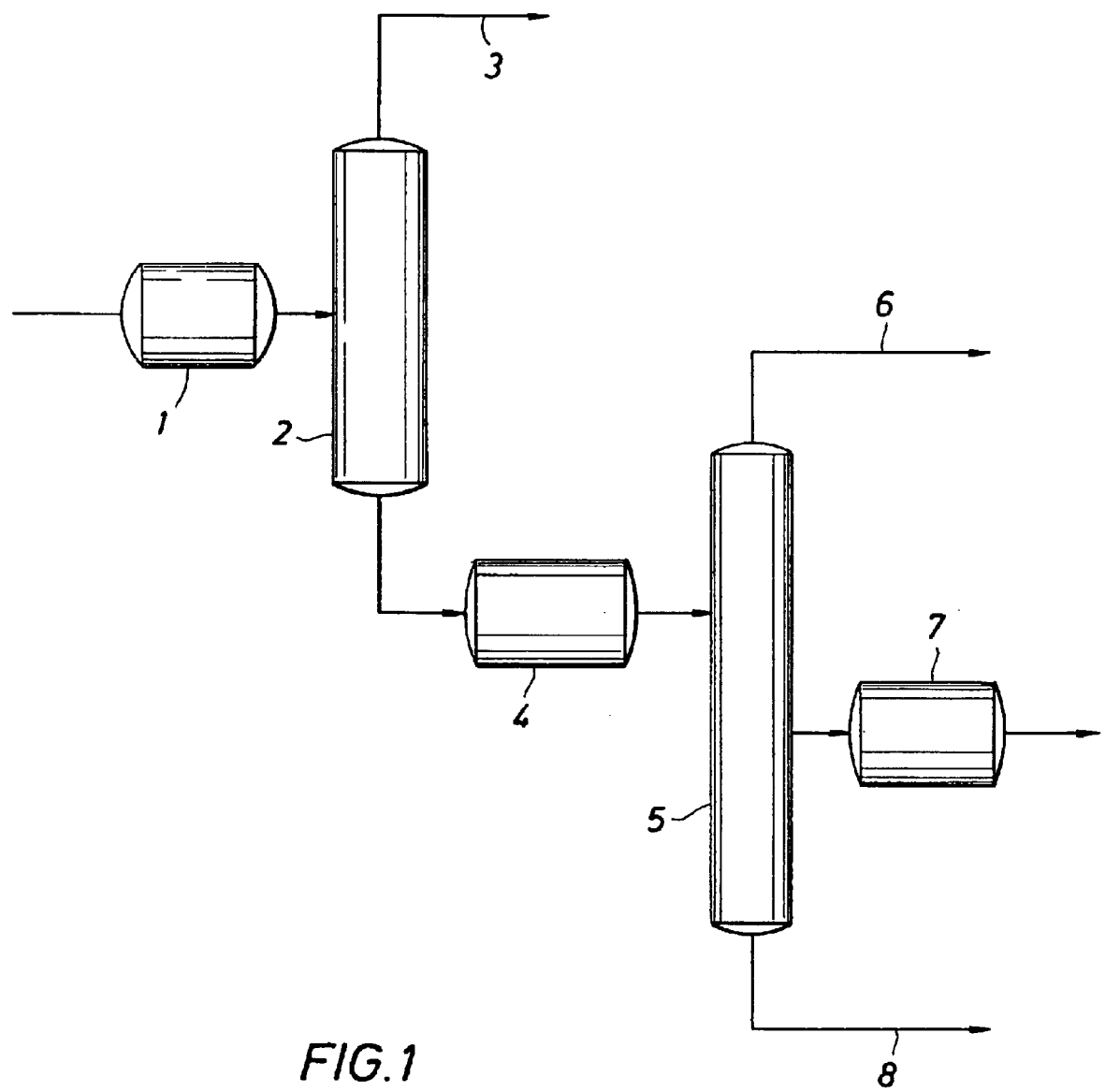
FIG. 1 is very simple schematic representation of an example of a simplified distillation scheme.

The 3-hydroxypropanal (HPA) aqueous solution which is the starting material of the present invention, can be produced by a number of different processes. The aforementioned U.S. Pat. Nos. 4,873,378, 4,873,379, 5,053,562, 5,030,766, 5,210,318, 5,256,827, 5,304,686, and 5,304,691, all of which are herein incorporated by reference, describe different methods for producing aqueous solutions of HPA. HPA can also be produced by hydration of acrolein in the presence of acidic catalysts. Processes for accomplishing this result are described in U.S. Pat. Nos. 5,426,249, 5,015,789, 5,171,898, 5,276,201, 5,334,778, and 5,364,987, all of which are herein incorporated by reference.

A preferred method for carrying out the entire process of the present invention is described in U.S. Pat. No. 5,786,524, which is herein incorporated by reference, and is generally as follows. Ethylene oxide (EO) is hydroformylated in a reactor such as a bubble column or agitated tank at about 200 to about 5000 psi (about 1380 to about 34,500 kPa) of syngas having a ratio of hydrogen to carbon monoxide of about 1:5 to about 25:1 at about 50 to about 110° C. in the presence of a hydroformylation catalyst at a concentration of about 0.05 to about 15 weight percent, more preferably about 0.05 to about 1 percent.

The hydroformylation reaction effluent is preferably extracted with a small amount of water at water-solvent ratios ranging from about 2:1 to about 1:20 at about 5 to about 55° C. under an atmosphere of greater than about 50 psi (350 kPa) carbon monoxide. The solvent layer containing more than about 90 percent of the catalyst in active form is recycled back to the hydroformylation reactor. The HPA is extracted in the water layer at a concentration of about 10 to about 45 weight percent.

The catalyst may be removed from this aqueous solution of HPA by any known means including first oxidizing the catalyst and then removing it utilizing an acid ion exchange resin. The ion exchange resin may be a weak or strong acid ion exchange resin. Examples include AMBERLYST® 15, 35, and XN-1010, AMBERLITE® IR-118, IRC76, A1200, DOWEX® 50×2-100 and 5×8-100, XL-383 and -386, plus BIO RAD® AG50W-X2 and AMBERSEP® 252H resins, or other strong (sulfonic) acid or weak (carboxylic) acid resins.

After neutralization of the aqueous solution of 3-hydroxypropanal, the aqueous solution is hydrogenated. This may be carried out by hydrogenation over a fixed bed of hydrogenation catalyst at typically about 100 to about 2000 psi (about 690 to about 13,800 kPa) of hydrogen. The hydrogenation catalyst can be any of those described in U.S. Pat. No. 5,786,524, which is herein incorporated by reference, including catalysts of a group VIII metal such as nickel, cobalt, ruthenium, platinum, or palladium. Initial hydrogenation is preferably conducted at about 40 to about 80° C. and the temperature is preferably increased to about 120 to about 175° C. to encourage the reaction of reactive components such as cyclic acetals to revert back to PDO. Finally, water and entrained light solvent and highly volatile impurities are distilled (overhead stream) from the crude PDO and the lower volatility components are also separated during distillation as the bottoms stream.

As shown in the exemplary simplified distillation scheme of FIG. 1, the aqueous PDO containing MW176 acetal flows into drying distillation column 2. Water and some high volatility materials are removed in the overhead stream 3 and the dried PDO with MW176 acetal from the distillate bottoms stream flows into distillation column 5. More high volatility materials are separated and leave through overhead stream 6 and the distillate bottoms stream 8 contains low volatility materials and some PDO as well as trace amounts of MW176 acetal. The recoverable PDO exits in the middle stream. The acid catalyst treatment may take place before drying in vessel 1 or it may take place after drying but before distillation in vessel 4 or it may take place after distillation in vessel 7. When the last embodiment is carried out, an additional distillation is required to separate the more volatile MW176 acetal reaction products from the PDO.

Crude PDO as described above sometimes exhibits high levels of MW176 cyclic acetal impurity. This impurity was found to be only marginally less volatile than PDO, which limits PDO recovery efficiencies. Given difficulty in separation from PDO, laboratory batch distillation was conducted to assess the relative volatilities of MW176 impurity and PDO. Approximately 85 grams of PDO tainted with this impurity and also a $C_5$ diol were refluxed at a nominal 10 mm Hg (1.3 kPa) pressure and 143° C. bottoms temperature. Ethylene glycol (EG) and butanediol markers were added at about 1 wt % to assist in assignment of relative volatilities. The results (Table 1) show both the MW176 acetal and $C_5$ diol to be heavier than PDO. Good agreement was obtained between measured vs. reported relative volatility of EG vs. PDO which indicates that equilibrium was indeed approached for these measurements.

TABLE 1

Relative Volatility[1]
BATCH DISTILLATION DATA:

| Species | Distillation bottoms wt % | Distillation tops wt % | Volatility ratio: t/b[2] |
|---|---|---|---|
| PDO | 97.88 | 98.09 | 1.00 |
| Ethylene glycol | 0.369 | 0.824 | 2.233 |
| $C_5$ diol | 0.326 | 0.280 | 0.859 |
| MW176 acetal | 0.055 | 0.047 | 0.855 |
| Butanediol | 1.375 | 0.762 | 0.554 |

[1]Reported relative volatility EG/PDO at 230° F. (110° C.) = 2.16
[2]t = distillation "tops" or "overhead product"
b = distillation "bottoms"

The MW102 acetal formed upon acid catalyzed decomposition of MW176 acetal is known to be much more volatile than PDO and hence can be readily separated from PDO with high efficiency. This result was expected basis the absence of hydroxyl groups in MW102 due to condensation elimination. While we do not wish to be bound by a specific mechanism, the following reactions may explain the degradation of MW176 acetal and formation of MW102 acetal (that can be readily separated from the PDO by distillation) and also the formation of MW132 acetal as observed in the experiments.

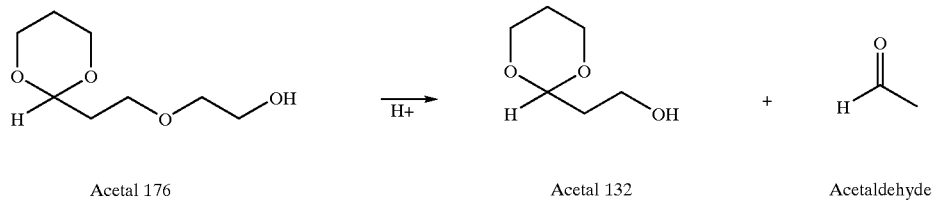

Acetal 176         Acetal 132         Acetaldehyde

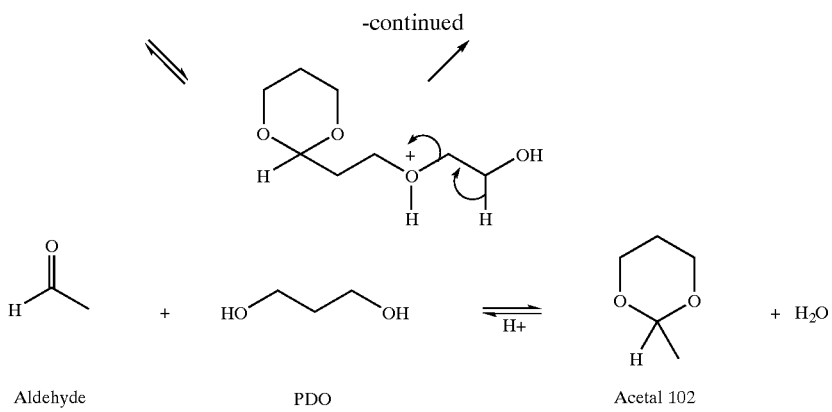

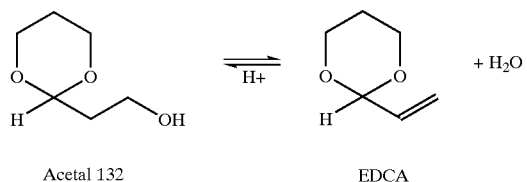

"De-ethoxylation" is known to occur under acidic conditions. Aldehydes readily condense with PDO under acidic conditions to form thermodynamically favored cyclic acetals, in this case, MW102 acetal.

An acid form cation exchange resin or an acidic zeolite also facilitates the removal of MW132 acetal via converion to 2-ethylene-1,3-dioxane cyclic acetal (EDCA) which is a substantially higher volatility material.

The crude PDO stream containing the undesirable MW176 acetal is treated with an acid form cation exchange resin or an acidic zeolite or soluble acid under conditions which favor the reaction schemes shown above. Batch or continuous flow processes may be used in any manner providing intimate contacting of the liquid stream with the solid acid purifier or the soluble acid. Typically, continuous contacting in a fixed, fluidized, or expanded bed will be preferred commercially, in either downflow or upflow operation or via a horizontal contactor. While the optimal size of the bed will depend upon the particle size and nature of the solid acid purifier employed, a typical design will entail a "weight hourly space velocity" (WHSV) between about 0.1 and about 10, with WHSV expressed as the mass flowrate of crude PDO per mass of solid acid purifier per hour. The optimal bed size and operating temperature are selected to effect a high level of conversion of MW176 acetal, while minimizing the oligomerization of PDO to other heavy ends components.

When acidic zeolites are employed as the solid acid purifier, a temperature in the range of about 40 to about 150° C., preferably about 60 to about 120° C., is typically desired. Temperatures of ambient to about 150° C. or lower temperatures (as low as ambient temperature to about 100° C.) may be employed with acid form cation exchange resins, which are indicated to be more active in removal of the MW176 impurity. When soluble acids are used, the temperature may be from about 20 to about 100° C.

The preferred zeolite catalysts contain one or more modified zeolites preferably in the acidic form. These zeolites should contain pore dimensions large enough to admit the entry of the acyclic or aliphatic compounds. The preferred zeolites include, for example, zeolites of the structural types MFI (e.g., ZSM-5), MEL (e.g., ZSM-11), FER (e.g., ferrierite and ZSM-35), FAU (e.g., zeolite Y), BEA (e.g., beta), MFS (e.g., ZSM-57), NES (e.g. NU-87), MOR (e.g. mordenite), CHA (e.g., chabazite), MTT (e.g., ZSM-23), MWW (e.g., MCM-22 and SSZ-25), EUO (e.g. EU-1, ZSM-50, and TPZ-3), OFF (e.g., offretite), MTW (e.g., ZSM-12) and zeolites ITQ-1, ITQ-2, MCM-56, MCM-49, ZSM-48, SSZ-35, SSZ-39 and zeolites of the mixed crystalline phases such as, for example, zeolite PSH-3. The structural types and references to the synthesis of the various zeolites can be found in the "Atlas of Zeolite Structure Types" (published on behalf of the Structure Commission of the International Zeolite Association), by W. M. Meier, D. H. Olson and Ch. Baerlocher, published by Butterworth-Heinemann, fourth revised edition, 1996. Structural types and references to the zeolites mentioned above are available on the World Wide Web at www.iza-structure.org Such zeolites are commercially available from Zeolyst International, Inc. and ExxonMobil Corporation. Additional examples of suitable zeolite catalysts can be found in U.S. Pat. Nos. 5,762,777; 5,808,167; 5,110,995; 5,874,646; 4,826,667; 4,439,409; 4,954,325; 5,236,575; 5,362,697; 5,827,491; 5,958,370; 4,016,245; 4,251,499; 4,795,623; 4,942,027 and WO99/35087, which are hereby incorporated by reference.

Other suitable catalysts include acid form cation exchange resins. These include the gel type or macroreticular (macroporous) ion exchange resins with sulfonic acid functional groups in acid form, wherein the sulfonic acid function is bonded directly or indirectly to an organic polymer backbone. Examples include: Rohm and Haas AMBERLITE® or AMBERLYST® A200, A252, IR-118, IR120, A15, A35, XN-1010, or uniform particle size A1200 resins; Dow MSC-1 or DOWEX® 50-series resins; SYBRON® C-249, C-267, CFP-110 resins; PUROLITE® C-100 or C-150 resins; RESINTECH® CG8; IWT C-211; SACMP; IWT C-381; and other comparable commercial resins. Another example of these cation exchange resins is NAFION® acidified perfluorinated polymer of sulphonic acid.

Soluble acids which can be used include $H_2SO_4$, $H_3PO_4$, HCl, and soluble sulfonic acids such as paratoluene sulfonic acid, benzene sulfonic acid, and methane sulfonic acid, etc. $H_2SO_4$ and soluble sulfonic acids are preferred. If these soluble acids are used, corrosion-resistant columns are highly preferred. The acid is removed with the heaviest components (heavy ends). The concentration of the acid is preferably about 0.1 to about 1.0 wt %.

EXAMPLES

Example 1

The results in Table 2 show that ambient temperature treatment of a PDO sample contaminated with MW176 acetal with acid-form USY-type zeolite was ineffective in reverting MW176 acetal. Room temperature reversion using strong acid resin A15 (Rohm and Haas AMBERLYST® 15) was demonstrated. High temperature treatment with the zeolite at 150° C. overnight resulted in elimination of MW176 with formation of 2-methyl-1,3-dioxane. However, formation of poly PDO (di-1,3-propylene glycol) and higher oligomers occurred at higher concentrations than the original MW176 acetal. Overall purity and yield was thus reduced, though the more difficult to separate MW176 acetal was eliminated.

Additional timed studies were conducted at 100° C. using the USY H+ form zeolite. The results show reactive conversion of the MW176 acetal, especially the first gc (gas chromatograph) peak MW176-1 which reacted to virtual completion within 5 hours (MW176 acetal shows up as three peaks in gc/mass spec analysis; the dominant MW176-1 peak described in Table 2 readily vanished during acid treatment experiments, while a second "isomer" appeared to be unreactive). Unlike the earlier test at 150° C., at 100° C. the reversion was selective with no measurable formation of di- or tri-1,3-propylene glycol via condensation of PDO.

A mordenite sample was inadvertently first tested in sodium form overnight at 150° C., giving copious amounts of new heavy ends byproducts, presumably via degradation of PDO. A sample of the acid-form mordenite heated with the same PDO overnight at 60° C. showed, however, essentially complete elimination of the MW176 acetal, with formation of the same 2-methyl-1,3-dioxane (MW102 acetal) and MW132 acetal impurities as observed with the USY type zeolite. The reversion was selective as no additional byproducts were observed. The performance of the acid-form mordenite was thus comparable with that of the USY acid-form zeolite. These results indicate an optimal temperature for complete or partial removal of the MW176 acetal, with minimal degradation of PDO to other byproducts.

Example 2

A study was conducted via contacting of PDO high in MW176 acetal impurity with a strong cation acid ion exchange resin (Rohm and Haas AMBERLYST® A35) at room temperature. The results shown in Table 3 indicate degradation of MW176 acetal, with formation of MW102 acetal, MW18 ($H_2O$), and MW132 acetal.

TABLE 3

Preliminary PDO Treatment Over A35 Resin at Room Temperature

| Name | MW | % wt Start | % wt End |
|---|---|---|---|
| 2-methyl cyclic acetal | 102 | 0.00 | 0.10 |
| cyclic acetal | 132 | 0.05 | 0.29 |
| cyclic acetal diol | 176 | 0.24 | 0.01 |
| water | 18 | 0.02 | 1.02 |
| PDO | 76 | 99.47 | 98.39 |
| other | 162 | 0.02 | 0.00 |
| other | 176 | 0.02 | 0.01 |
|  |  | 99.81 | 99.83 |
| mole balance |  | 1.31 | 1.35 |

Solid acid treatment of PDO tainted with MW176 acetal can degrade this impurity into lighter components (MW102 nonhydroxylated acetal) which are readily separable via distillation. Strong cation acid ion exchange resins can revert the MW176 acetal at room temperature. Acidic zeolites can also revert the MW176 acetal at a higher temperature. At still higher temperatures (as demonstrated for 150° C.), PDO is condensed by the acidic zeolites to poly 1,3-propylene glycols, leading to yield loss and lower purity.

We claim:

1. In a process for producing 1,3-propanediol where an aqueous solution of 3-hydroxypropanal is formed, the 3-hydroxypropanal is hydrogenated to form a crude 1,3-propanediol mixture comprising 1,3-propanediol, water, MW176 cyclic acetal, and high and low volatility materials, the crude 1,3-propanediol mixture is dried to produce a first overhead stream comprising water and a first distillate bottoms stream comprising 1,3-propanediol, MW176 cyclic

TABLE 2

Solid Acid Purification of MW176 Contaminated PDO

| Time hours | Catalyst | Temp ° C. | Catalyst wt % | MW176 wt % | MW132 wt % | MW102 wt % | RT26.8 MW176-1 wt % | di-PDO wt % | tri-PDO wt % | other new H.E. wt % |
|---|---|---|---|---|---|---|---|---|---|---|
| 0 | none (feed) | 25 | 0.0 | 0.240 | 0.050 | 0.000 | 0.168 | 0.000 | 0.000 | 0.0 |
| 24 | Acid resin A35 | 25 | 4.0 | 0.010 | 0.290 | 0.100 | 0 | 0.000 | 0.000 | 0.0 |
| 24 | USY H+ zeolite | 25 | 4.0 | 0.240 | 0.050 | 0.000 | na | 0.000 | 0.000 | 0.0 |
| 24 | USY H+ zeolite | 150 | 4.0 | 0.010 | 0.041 | 0.124 | 0.002 | 0.545 | 0.514 | 0.0 |
| 0 | none (feed) | 25 | 0.0 | 0.237 | 0.093 | 0.000 | 0.161 | 0.000 | 0.000 | 0.0 |
| 18 | Acid resin A15 | 25 | 10.0 | 0.005 | 0.402 | 0.161 | 0.002 | 0.000 | 0.000 | 0.0 |
| 18 | Acid A15 + 15% $H_2O$ | 25 | 10.0 | 0.01 | 0.111 | 0.048 | 0.005 | 0.000 | 0.000 | 0.0 |
| 27 | Na-mordenite | 150 | 10.0 | 0.016 | 0.084 | 0.018 | 0.013 | 0.000 | 0.000 | 20.5 |
| 22 | H+ mordenite | 60 | 3.6 | 0.017 | 0.431 | 0.143 | 0.005 | 0.000 | 0.000 | 0.0 |
| 0 | none (feed) | 100 | 0.0 | 0.237 | 0.093 | 0.000 | 0.161 | 0.000 | 0.000 | 0.0 |
| 1 | USY H+ zeolite | 100 | 10.0 | 0.136 | 0.209 | 0.075 | 0.082 | 0.000 | 0.000 | 0.0 |
| 3 | USY H+ zeolite | 100 | 10.0 | 0.048 | 0.330 | 0.127 | 0.018 | 0.000 | 0.000 | 0.0 |
| 5 | USY H+ zeolite | 100 | 10.0 | 0.033 | 0.371 | 0.142 | 0.004 | 0.000 | 0.000 | 0.0 |
| 27 | USY H+ zeolite | 100 | 10.0 | 0.030 | 0.351 | 0.147 | 0.003 | 0.000 | 0.000 | 0.0 |

USY H+ zeolite = CBV-500-X16 LR22765 (Apr. 2, 2000)
H-mordenite = LR23768-128 (Jan. 28, 2000)

acetal, and high and low volatility materials, and the first distillate bottoms stream is distilled to produce a second overhead stream comprising high volatility materials, a middle stream comprising 1,3-propanediol and MW176 acetal, and a second distillate bottoms stream comprising 1,3-propanediol and low volatility materials, the improvement which comprises contacting said crude 1,3-propanediol mixture, prior to drying thereof, with an acidic zeolite at about 40 to about 150° C. to convert the MW176 cyclic acetal to more volatile materials which can be easily separated from 1,3-propanediol by distillation.

2. The process of claim 1 wherein the temperature is from about 60 to about 120° C. whereby the production of color-producing impurities and dimer and higher oligomers of 1,3-propanediol is minimized.

3. In a process for producing 1,3-propanediol where an aqueous solution of 3-hydroxypropanal is formed, the 3-hydroxypropanal is hydrogenated to form a crude 1,3-propanediol mixture comprising 1,3-propanediol, water, MW176 cyclic acetal, and high and low volatility materials, the crude 1,3-propanediol mixture is dried to produce a first overhead stream comprising water and a first distillate bottoms stream comprising 1,3-propanediol, MW176 cyclic acetal, and high and low volatility materials, and the first distillate bottoms stream is distilled to produce a second overhead stream comprising high volatility materials, a middle stream comprising 1,3-propanediol and MW176 acetal, and a second distillate bottoms stream comprising 1,3-propanediol and low volatility materials, the improvement which comprises contacting said crude 1,3-propanediol mixture, prior to drying thereof, with an acid form cationic exchange resin at ambient to about 150° C. to convert the MW176 cyclic acetal to more volatile materials which can be easily separated from 1,3-propanediol by distillation.

4. The process of claim 3 wherein the temperature is from ambient to about 100° C.

5. In a process for producing 1,3-propanediol where an aqueous solution of 3-hydroxypropanal is formed, the 3-hydroxypropanal is hydrogenated to form a crude 1,3-propanediol mixture comprising 1,3-propanediol, water, MW176 cyclic acetal, and high and low volatility materials, the crude 1,3-propanediol mixture is dried to produce a first overhead stream comprising water and a first distillate bottoms stream comprising 1,3-propanediol, MW176 cyclic acetal, and high and low volatility materials, and the first distillate bottoms stream is distilled to produce a second overhead stream comprising high volatility materials, a middle stream comprising 1,3-propanediol and MW176 acetal, and a second distillate bottoms stream comprising 1,3-propanediol and low volatility materials, the improvement which comprises contacting said crude 1,3-propanediol mixture, prior to drying thereof, with a soluble acid at a temperature of about 20 to about 100° C. to convert the MW176 cyclic acetal to more volatile materials which can be easily separated from 1,3-propanediol by distillation.

6. In a process for producing 1,3-propanediol where an aqueous solution of 3-hydroxypropanal is formed, the 3-hydroxypropanal is hydrogenated to form a crude 1,3-propanediol mixture comprising 1,3-propanediol, water, MW176 cyclic acetal, and high and low volatility materials, the crude 1,3-propanediol mixture is dried to produce a first overhead stream comprising water and a first distillate bottoms stream comprising 1,3-propanediol, MW176 cyclic acetal, and high and low volatility materials, and the first distillate bottoms stream is distilled to produce a second overhead stream comprising high volatility materials, a middle stream comprising 1,3-propanediol and MW176 acetal, and a second distillate bottoms stream comprising 1,3-propanediol and low volatility materials, the improvement which comprises contacting said first distillate bottoms stream, prior to distillation thereof, with an acidic zeolite at about 40 to about 150° C. to convert the MW176 cyclic acetal to more volatile materials which can be easily separated from 1,3-propanediol by distillation.

7. The process of claim 6 wherein the temperature is from about 60 to about 120° C. whereby the production of color-producing impurities and dimer and higher oligomers of 1,3-propanediol is minimized.

8. In a process for producing 1,3-propanediol where an aqueous solution of 3-hydroxypropanal is formed, the 3-hydroxypropanal is hydrogenated to form a crude 1,3-propanediol mixture comprising 1,3-propanediol, water, MW176 cyclic acetal, and high and low volatility materials, the crude 1,3-propanediol mixture is dried to produce a first overhead stream comprising water and a first distillate bottoms stream comprising 1,3-propanediol, MW176 cyclic acetal, and high and low volatility materials, and the first distillate bottoms stream is distilled to produce a second overhead stream comprising high volatility materials, a middle stream comprising 1,3-propanediol and MW176 acetal, and a second distillate bottoms stream comprising 1,3-propanediol and low volatility materials, the improvement which comprises contacting said first distillate bottoms stream, prior to distillation thereof, with an acid form cationic exchange resin at ambient to about 150° C. to convert the MW176 cyclic acetal to more volatile materials which can be easily separated from 1,3-propanediol by distillation.

9. The process of claim 8 wherein the temperature is from ambient to about 100° C.

10. In a process for producing 1,3-propanediol where an aqueous solution of 3-hydroxypropanal is formed, the 3-hydroxypropanal is hydrogenated to form a crude 1,3-propanediol mixture comprising 1,3-propanediol, water, MW176 cyclic acetal, and high and low volatility materials, the crude 1,3-propanediol mixture is dried to produce a first overhead stream comprising water and a first distillate bottoms stream comprising 1,3-propanediol, MW176 cyclic acetal, and high and low volatility materials, and the first distillate bottoms stream is distilled to produce a second overhead stream comprising high volatility materials, a middle stream comprising 1,3-propanediol and MW176 acetal, and a second distillate bottoms stream comprising 1,3-propanediol and low volatility materials, the improvement which comprises contacting said first distillate bottoms stream, prior to distillation thereof, with a soluble acid at a temperature of about 20 to about 100° C. to convert the MW176 cyclic acetal to more volatile materials which can be easily separated from 1,3-propanediol by distillation.

11. In a process for producing 1,3-propanediol where an aqueous solution of 3-hydroxypropanal is formed, the 3-hydroxypropanal is hydrogenated to form a crude 1,3-propanediol mixture comprising 1,3-propanediol, water, MW176 cyclic acetal, and high and low volatility materials, the crude 1,3-propanediol mixture is dried to produce a first overhead stream comprising water and a first distillate bottoms stream comprising 1,3-propanediol, MW176 cyclic acetal, and high and low volatility materials, and the first distillate bottoms stream is distilled to produce a second overhead stream comprising high volatility materials, a middle stream comprising 1,3-propanediol and MW176 acetal, and a second distillate bottoms stream comprising 1,3-propanediol and low volatility materials, the improvement which comprises contacting said middle stream with an acidic zeolite at about 40 to about 150° C. to convert the MW176 cyclic acetal to more volatile materials which can be easily separated from 1,3-propanediol by distillation.

12. The process of claim 11 wherein the temperature is from about 60 to about 120° C. whereby the production of color-producing impurities and dimer and higher oligomers of 1,3-propanediol is minimized.

13. In a process for producing 1,3-propanediol where an aqueous solution of 3-hydroxypropanal is formed, the 3-hydroxypropanal is hydrogenated to form a crude 1,3-propanediol mixture comprising 1,3-propanediol, water, MW176 cyclic acetal, and high and low volatility materials, the crude 1,3-propanediol mixture is dried to produce a first overhead stream comprising water and a first distillate bottoms stream comprising 1,3-propanediol, MW176 cyclic acetal, and high and low volatility materials, and the first distillate bottoms stream is distilled to produce a second overhead stream comprising high volatility materials, a middle stream comprising 1,3-propanediol and MW176 acetal, and a second distillate bottoms stream comprising 1,3-propanediol and low volatility materials, the improvement which comprises contacting said middle stream with an acid form cationic exchange resin at ambient to about 150° C. to convert the MW176 cyclic acetal to more volatile materials which can be easily separated from 1,3-propanediol by distillation.

14. The process of claim 13 wherein the temperature is from ambient to about 100° C.

15. In a process for producing 1,3-propanediol where an aqueous solution of 3-hydroxypropanal is formed, the 3-hydroxypropanal is hydrogenated to form a crude 1,3-propanediol mixture comprising 1,3-propanediol, water, MW176 cyclic acetal, and high and low volatility materials, the crude 1,3-propanediol mixture is dried to produce a first overhead stream comprising water and a first distillate bottoms stream comprising 1,3-propanediol, MW176 cyclic acetal, and high and low volatility materials, and the first distillate bottoms stream is distilled to produce a second overhead stream comprising high volatility materials, a middle stream comprising 1,3-propanediol and MW176 acetal, and a second distillate bottoms stream comprising 1,3-propanediol and low volatility materials, the improvement which comprises contacting said middle stream with a soluble acid at a temperature of about 20 to about 100° C. to convert the MW176 cyclic acetal to more volatile materials which can be easily separated from 1,3-propanediol by distillation.

\* \* \* \* \*